(12) United States Patent
Pan et al.

(10) Patent No.: US 7,814,910 B2
(45) Date of Patent: Oct. 19, 2010

(54) NOSE CAP

(75) Inventors: Neng-Yu Pan, Tu-Cheng (TW);
Yao-Ming Cheng, Tu-Cheng (TW);
I-Chung Chen, Tu-Cheng (TW)

(73) Assignee: Apex Medical Corp., Taipei Hsien (TW)

( * ) Notice: Subject to any disclaimer, the term of this patent is extended or adjusted under 35 U.S.C. 154(b) by 857 days.

(21) Appl. No.: 11/701,101

(22) Filed: Jan. 31, 2007

(65) Prior Publication Data

US 2008/0178887 A1    Jul. 31, 2008

(51) Int. Cl.
*A62B 18/08* (2006.01)
*A62B 18/02* (2006.01)

(52) U.S. Cl. .............................. 128/206.24; 128/206.21; 128/207.13

(58) Field of Classification Search ............ 128/200.24, 128/201.22–201.24, 203.12, 203.29, 204.18, 128/205.25, 206.12, 206.21–206.24, 206.28, 128/207.11–207.14, 207.18
See application file for complete search history.

(56) References Cited

U.S. PATENT DOCUMENTS

| | | | | |
|---|---|---|---|---|
| 4,574,799 A | * | 3/1986 | Warncke | 128/206.24 |
| 6,135,109 A | * | 10/2000 | Blasdell et al. | 128/206.28 |
| 6,796,308 B2 | | 9/2004 | Gunaratnam et al. | |
| 6,871,649 B2 | | 3/2005 | Kwok et al. | |
| 7,007,696 B2 | * | 3/2006 | Palkon et al. | 128/207.13 |
| 7,069,933 B2 | | 7/2006 | Kwok et al. | |
| 7,546,837 B2 | * | 6/2009 | Busch et al. | 128/206.24 |
| D597,199 S | * | 7/2009 | Smart et al. | D24/110.1 |
| 2004/0094159 A1 | * | 5/2004 | Kwok et al. | 128/206.24 |
| 2005/0257792 A1 | * | 11/2005 | Wixey et al. | 128/206.24 |
| 2006/0249159 A1 | * | 11/2006 | Ho et al. | 128/207.13 |
| 2008/0178887 A1 | * | 7/2008 | Pan et al. | 128/207.13 |

* cited by examiner

*Primary Examiner*—Justine R Yu
*Assistant Examiner*—Rachel T Young
(74) *Attorney, Agent, or Firm*—William E. Pelton, Esq.; Cooper & Dunham LLP

(57) ABSTRACT

A nose cap includes a hollow body having a first opening, a second opening communicating with the first opening via a first passage and an outer covering having a third opening communicating with the first opening of the hollow body and a fourth opening communicating with the third opening via a second passage. An air chamber is formed between the hollow body and the outer covering after extension of the hollow body into the second passage. The air chamber is able to provide comfort to a patient.

3 Claims, 5 Drawing Sheets

NOSE CAP

BACKGROUND OF THE INVENTION

1. Field of the Invention

The present invention relates to a nose cap, and more particularly to nose cap having therein an air chamber so as to provide comfort to the user.

2. Description of the Prior Art

A nose cap is for a patient having trouble breathing himself/herself or needing a large quantity of pure oxygen such that after the patient wears the nose cap, air or oxygen is supplied to the patient.

With reference to FIGS. 4 and 5, a conventional nose cap (40) is shown. The conventional nose cap (40) has a hollow body (41), a first opening (411) defined at one side of the hollow body (41), a buffering layer (412) formed between the hollow body (41) and the first opening (411), a second opening (413) formed on the other side of the hollow body (41) to communicate with the first opening (411), an inward extending supporting layer (414) formed on a peripheral edge of the second opening (413), an engagement layer (415) integrally extending from an outer face of the supporting layer (414) and a reduced opening (416) defined by an inward extending edge of the engagement layer (415). It is noted that an open space (417) is defined between the inward supporting layer (414) and the engagement layer (415).

When the nose cap (40) of this type is in use, the user's nose is extended into the reduced opening (416) and the engagement layer (415) is in full engagement with the patient's nose. The supporting layer (414) is provided to support and maintain the integrity of the entire nose cap (40) such that it is learned that a material used to make the supporting layer (414) is not the same as that for the engagement layer (415). However, the material for the engagement layer (415) must be soft and elastic so that the engagement layer (415) is able to be in full engagement with the patient's nose. But still, the open space (417) between the supporting layer (414) and the engagement layer (415) functions as a buffer when the nose cap (40) is worn by the patient. Because the open space (417) is limited within a small area, when the engagement layer (415) engages with the patient's nose, the patient might feel uncomfortable. Also, the sealing effect of the engagement layer (415) to the patient's nose is not good as expected for the limited open space (417).

To overcome the shortcomings, the present invention tends to provide an improved nose cap to mitigate the aforementioned problems.

SUMMARY OF THE INVENTION

The primary objective of the present invention is to provide an improved nose cap having an air chamber defined therein so as to provide comfort to the user.

In order to accomplish the aforementioned objective, the nose cap of the present invention has a hollow body and an outer covering having the hollow body received therein so that an air chamber is defined between the hollow body and the outer covering to provide comfort to the user.

Other objects, advantages and novel features of the invention will become more apparent from the following detailed description when taken in conjunction with the accompanying drawings.

DETAILED DESCRIPTION OF THE PREFERRED EMBODIMENT

Figure 1:
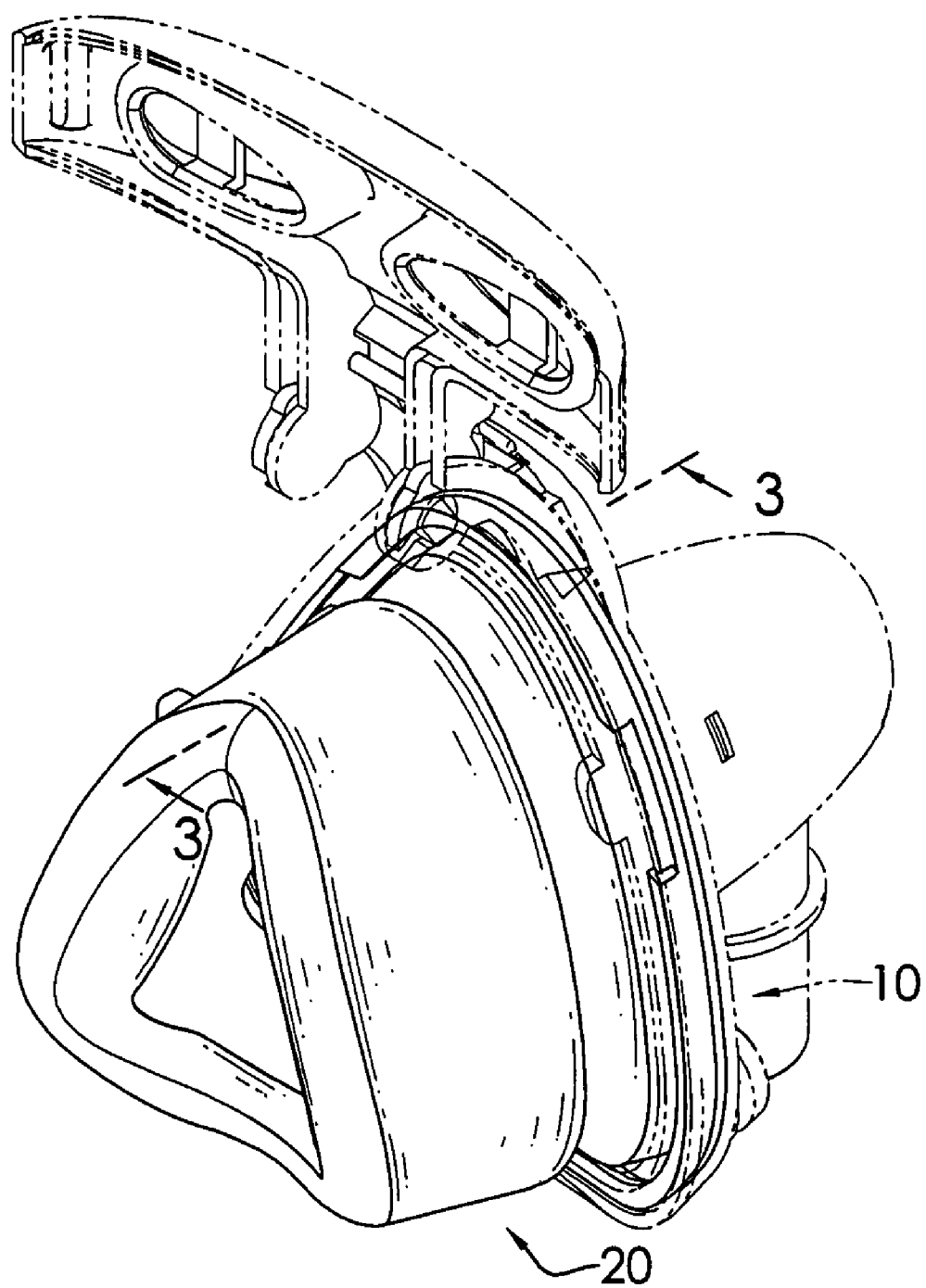
FIG. 1 is a perspective view of the nose cap of the present invention.
Figure 2:
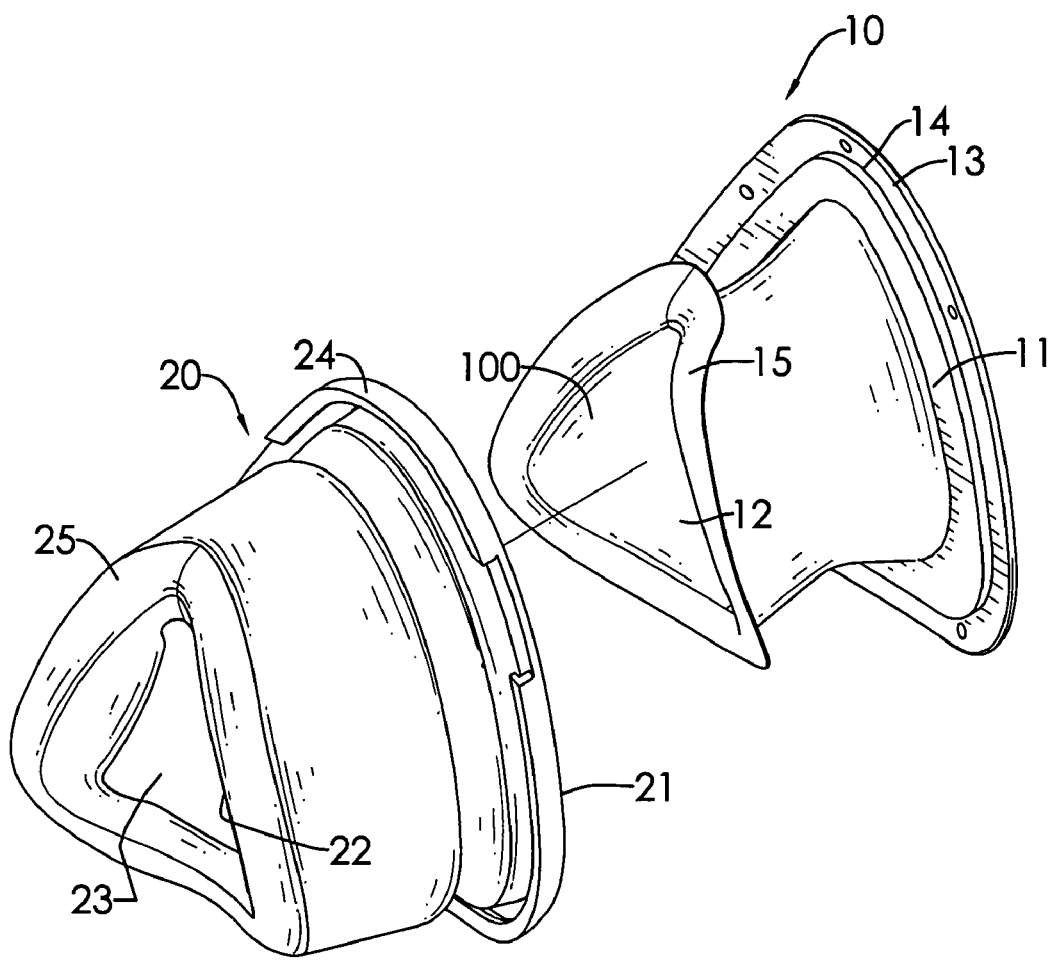
FIG. 2 is an exploded perspective view of the nose cap of the present invention.

With reference to FIGS. 1 and 2, it is noted that the nose cap in accordance with the present invention includes a hollow body (10) and an outer covering (20).

The hollow body (10) has a first opening (11), a second opening (12) communicating with the first opening (11) via a first passage (100), an engagement surface (13) formed on a peripheral face defining the first opening (11), a step (14) formed on a joint between the engagement surface (13) and the hollow body (10) and a flared surface (15) formed on a peripheral face defining the second opening (12).

The outer covering (20) includes a third opening (21) defined in one side of the outer covering (20) and communicating with the first opening (11) of the hollow body (10), a fourth opening (22) defined in other side of the outer covering (20) to be opposite to the third opening (21) and communicate with the second opening (12), the fourth opening (22) communicating with the third opening (21) via a second passage (23), a flange (24) formed on a peripheral edge defining the third opening (21) and an inward sealing surface (25) formed on a peripheral edge defining the fourth opening (22).

Figure 3:
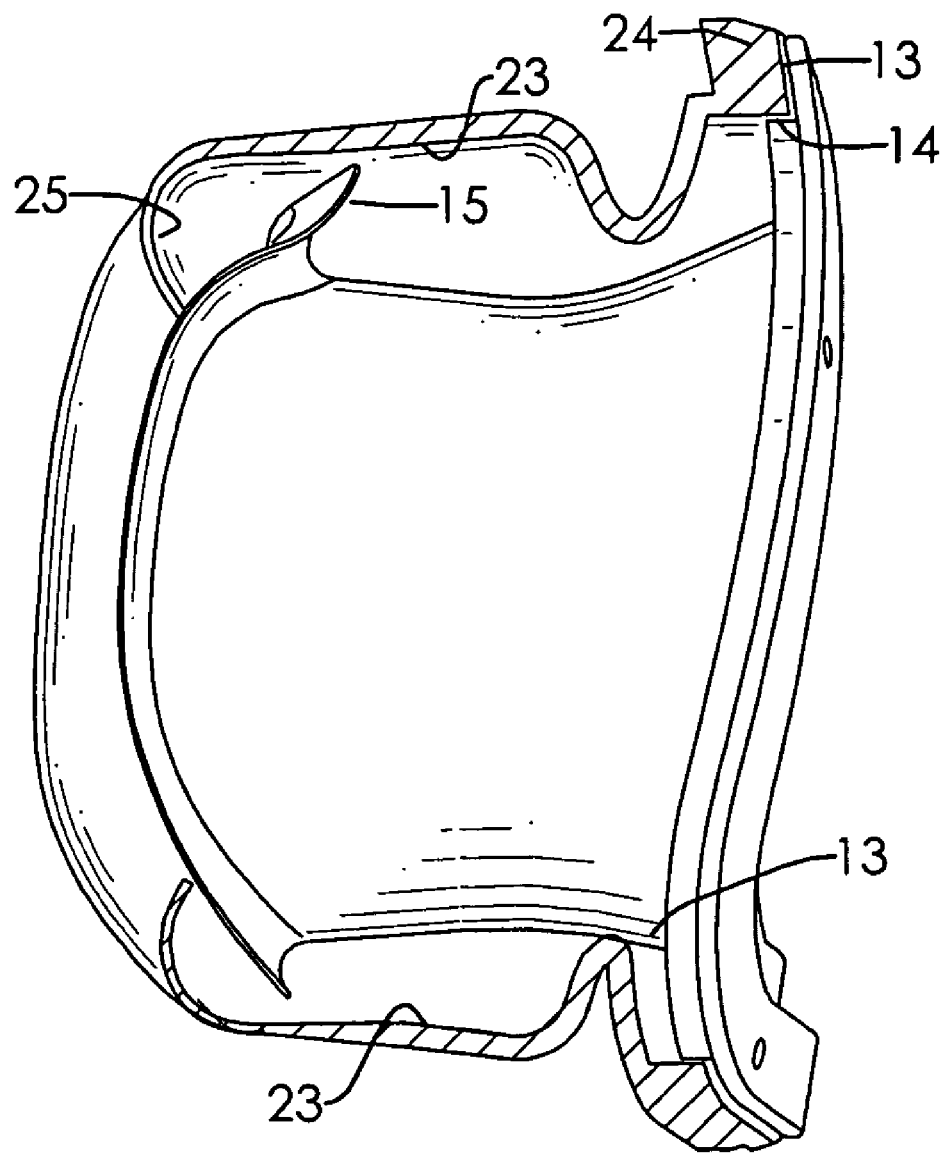
FIG. 3 is a cross sectional view of the nose cap by taking line 3-3 in FIG. 1.
Figure 4:
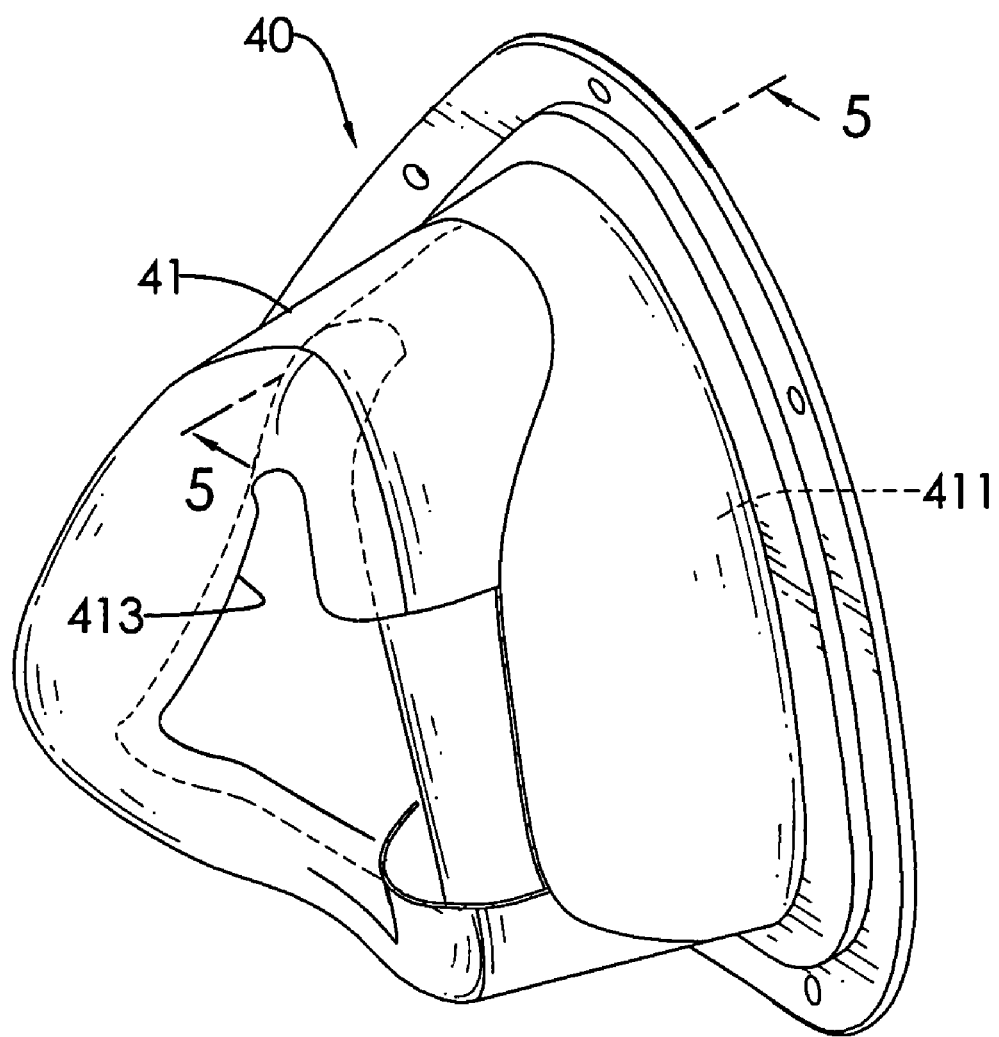
FIG. 4 is a perspective view of the conventional nose cap.
Figure 5:
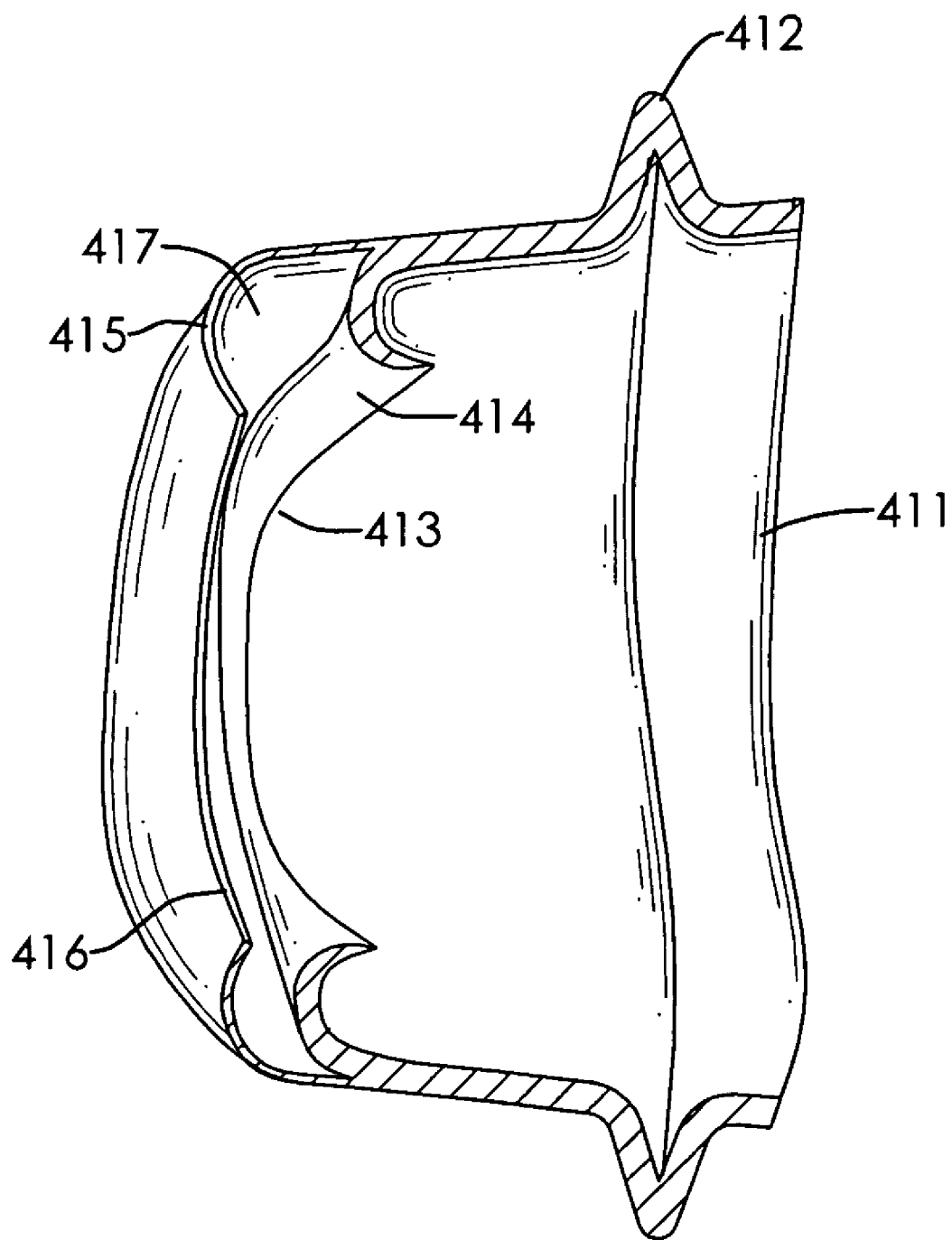
FIG. 5 is a cross sectional view of the nose cap by taking line 5-5 in FIG. 4.

With reference to FIG. 3, it is noted that when the nose cap is to be in application, the hollow body (10) is extended into the second passage (23) to allow the flared surface (15) to abut an inner side face of the inward sealing surface (25). Meanwhile, the flange (24) is engaged with the engagement surface (13) and abutted a side face of the step (14).

Therefore, it is noted that a closed air chamber is defined between the hollow body (10) and the outer covering (20). With the provision of the air chamber, when the nose cap of the present invention is worn by the patient, the closed air chamber is able to provide comfort to the patient.

It is also learned that when the nose cap of the present invention is produced, because the hollow body (10) and the outer covering (20) may be made of different materials and they are connected together after manufacture, there is not need for integration. That is, the outer covering (20) is still separate from the hollow body (10). Unlike the present invention, the conventional nose cap requires an integration process to allow the engagement layer (415) to be integrally extending out from the outer face of the inward supporting layer (414), which is an expensive and tiring process.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A nose cap comprising:

a hollow body having a first opening, a second opening communicating with the first opening via a first passage; and an outer covering having a third opening communicating with the first opening of the hollow body and a fourth opening communicating with the third opening via a second passage such that after extension of the hollow body into the second passage, an air chamber is defined between the hollow body and the outer covering to provide comfort to a patient, wherein a flared surface is formed on and protrudes outward from a peripheral edge defining the second opening; and an inward sealing surface is formed on and protrudes inward from a peripheral edge defining the fourth opening, a free end of the inward sealing surface engaging an outer face of the flared surface so that the air chamber is formed between the hollow body and the outer covering.

2. The nose cap as claimed in claim 1, wherein an engagement surface is formed on and protrudes outward from a peripheral edge defining the first opening and a step is formed between the engagement surface and the hollow body, and a flange is formed on and protrudes outward from a peripheral edge defining the third opening, the flange abutting a side face of the step and engaging the engagement surface.

3. The nose cap as claimed in claim 2, wherein the air chamber is formed around the hollow body and between the hollow body and the outer covering.

* * * * *